United States Patent
Mo et al.

(10) Patent No.: US 6,176,143 B1
(45) Date of Patent: *Jan. 23, 2001

(54) METHOD AND APPARATUS FOR ESTIMATION AND DISPLAY OF SPECTRAL BROADENING ERROR MARGIN FOR DOPPLER TIME-VELOCITY WAVEFORMS

(75) Inventors: Larry Y. L. Mo, Waukesha, WI (US); Scott D. Otterson, Seattle, WA (US)

(73) Assignee: General Electric Company, Milwaukee, WI (US)

( * ) Notice: Under 35 U.S.C. 154(b), the term of this patent shall be extended for 0 days.

This patent is subject to a terminal disclaimer.

(21) Appl. No.: 08/982,065

(22) Filed: Dec. 1, 1997

(51) Int. Cl.[7] ........................................ G01F 1/66

(52) U.S. Cl. ......................................... 73/861.25

(58) Field of Search .................... 73/861.25; 600/454; 128/661.08

(56) References Cited

U.S. PATENT DOCUMENTS

| 5,287,753 | 2/1994 | Routh et al. | 73/861.25 |
| 5,606,972 | 3/1997 | Routh | 128/661.09 |
| 5,935,074 | * 8/1999 | Mo et al. | 600/454 |

OTHER PUBLICATIONS

Newhouse et al., "The dependence of ultrasound Doppler bandwidth on beam geometry," IEEE Trans. Sonics and Ultrasonics, vol. su–27, No. 2, pp. 50–59 (1980).

Newhouse et al., "Invariance of Doppler bandwidth with flow axis displacement," Proc. IEEE Ultrasonics Symp., pp. 1533–1536 (1990).

Newhouse et al., "Study of vector flow estimation with transverse Doppler," Proc. IEEE Ultrasonics Symp., pp. 1259–1263 (1991).

Tortoli et al., "Invariance of the Doppler bandwidth with range cell size above a critical beam–to–flow angle," IEEE Trans. Ultrason., Ferroelec. & Freq. Control, vol. 40, No. 4, pp. 381–386 (1993).

Wilson, "Description of broad–band pulsed Doppler ultrasound processing using the two–dimensional Fourier transform," Ultrasonic Imag., vol. 13, pp. 301–315 (1991).

Winkler et al., "Correction of intrinsic spectral broadening errors in Doppler peak velocity measurements made with phased sector and linear array transducers," Ultrasound Med. Biol., vol. 21, No. 8, pp. 1029–1035 (1995).

Bascom et al., "Influence of spectral broadening on continuous wave Doppler ultrasound spectra: a geometric approach," Ultrasound Med. Biol., vol. 12, No. 5, pp. 387–395 (1986).

Bascom et al., "Problems in the quantitative assessment of pulsed Doppler spectra," Proc. 2th Ann. Conf. IEEE Eng. Med. Biol. Soc., Philadelphia, pp. 557–559 (1990).

Daigle et al., "Overestimation of velocity and frequency values by multielement linear array Dopplers," J. Vasc. Technology, vol. 14, No. 5, pp. 206–213 (1990).

(List continued on next page.)

Primary Examiner—Benjamin R. Fuller
Assistant Examiner—Jewel V. Thompson
(74) Attorney, Agent, or Firm—Dennis M. Flaherty; Christian G. Cabou; Phyllis Y. Price

(57) ABSTRACT

A method of calibrating Doppler time-velocity waveforms obtained using a duplex ultrasound scanner. A spectral broadening error margin for the maximum velocity waveform is determined based on a unified theory of intrinsic spectral broadening for pulsed Doppler signals. The error margin is colorized or highlighted in the Doppler waveform display.

11 Claims, 3 Drawing Sheets

OTHER PUBLICATIONS

Halberg et al., "Extraction of blood flow information using Doppler–shifted ultrasound," Hewlett–Packard J., pp. 35–40 (Jun. 1986).

Hoskins et al., "Velocity estimation using Duplex scanners," Ultrasound Med. Biol., Letters to the Editor, vol. 17, No. 2, pp. 195–198 (1991).

Kristoffersen et al., "A time–shared ultrasound Doppler measurement and 2–D imaging system," IEEE Trans. Biomed. Engng., vol. 35, No. 5, pp. 285–295 (1988).

Magnin, "Doppler effect: History and theory," Hewlett–Packard J., pp. 26–31 (Jun. 1986).

Mo et al., "Comparison of four digital maximum frequency estimators for Doppler ultrasound," Ultrasound Med. Biol., vol. 14, No. 5, pp. 355–363 (1988).

\* cited by examiner

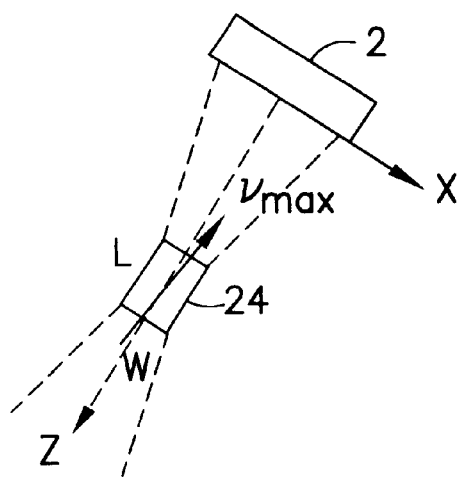
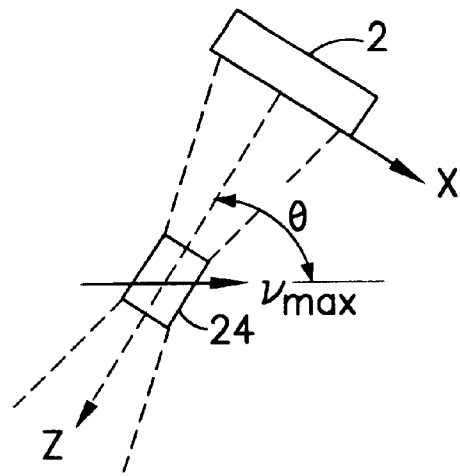
FIG.2A  FIG.2B
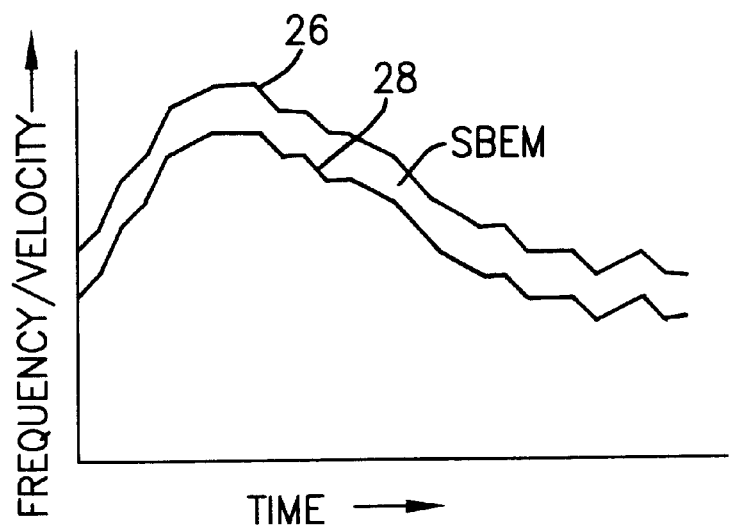
FIG.3

METHOD AND APPARATUS FOR ESTIMATION AND DISPLAY OF SPECTRAL BROADENING ERROR MARGIN FOR DOPPLER TIME-VELOCITY WAVEFORMS

FIELD OF THE INVENTION

This invention relates to ultrasonic diagnostic systems which measure the velocity of blood flow using spectral Doppler techniques. In particular, the invention relates to the continuous display of such information, including maximum and mean blood flow velocities.

BACKGROUND OF THE INVENTION

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency shift translates into the velocity of the blood flow.

In state-of-the-art ultrasonic scanners, the pulsed or continuous wave (CW) Doppler waveform is computed and displayed in real-time as a grey-scale spectrogram of velocity versus time with the grey-scale intensity (or color) modulated by the spectral power. The data for each spectral line comprises a multiplicity of frequency data bins for different frequency intervals, the spectral power data in each bin for a respective spectral line being displayed in a respective pixel of a respective column of pixels on the display monitor. Each spectral line represents an instantaneous measurement of blood flow.

FIG. 1 is a block diagram of the basic signal processing chain in a conventional spectral Doppler mode. An ultrasound transducer array 2 is activated to transmit by a transmit ultrasound burst which is fired repeatedly at a pulse repetition frequency (PRF). The PRF is typically in the kilohertz range. The return RF signals are detected by the transducer elements and then formed into a receive beam by a beamformer 4. For a digital system, the summed RF signal from each firing is demodulated by demodulator 6 into its in-phase and quadrature (I/Q) components. The I/Q components are integrated (summed) over a specific time interval and then sampled by block 8. The summing interval and transmit burst length together define the length of the sample volume as specified by the user. The "sum and dump" operation effectively yields the Doppler signal backscattered from the sample volume. The Doppler signal is passed through a wall filter 10 which rejects any clutter in the signal corresponding to stationary or very slow moving tissue. The filtered output is then fed into a spectrum analyzer 12, which typically takes Fast Fourier Transforms (FFTs) over a moving time window of 64 to 128 samples. Each FFT power spectrum is compressed (block 14) and mapped (block 16) to a grey scale for display on monitor 18 as a single spectral line at a particular time point in the Doppler velocity (frequency) versus time spectrogram.

The automatic Doppler waveform tracing (block 20) is performed after the FFT power spectrum x is compressed in accordance with a compression function h(x)=y and converted to grey map values in accordance with a mapping g(y)=z. The computed maximum/mean velocity traces are usually presented as overlay information on the spectrogram display. Whereas the mean frequency or velocity is defined by the first moment of the Doppler spectrum, the maximum frequency can be challenging to detect in a consistent manner, especially under weak SNR conditions.

One of the primary advantages of Doppler ultrasound is that it can provide noninvasive and quantitative measurements of blood flow in vessels. Given the angle θ between the insonifying beam and the flow axis, which is usually specified by rotating a cursor line in the B-mode image of a duplex scan, the magnitude of the velocity vector can be determined by the standard Doppler equation:

$$v = cf_d/(2f_0 \cos \theta)$$

where c is the speed of sound in blood, $f_0$ is the transmit frequency and $f_d$ is the motion-induced Doppler frequency shift in the backscattered ultrasound. In practice an intensity-modulated Doppler frequency versus time spectogram is displayed since the Doppler sample volume or range cell generally contains a distribution of velocities that can vary with time. Of special importance is the maximum frequency ($f_{max}$) waveform or "envelope" of the Doppler spectrogram, because its value at different points in the cardiac cycle is used in a number of diagnostic indices. In fact, it has been reported that an abnormally high $f_{max}$ or $v_{max}$ at peak systole alone is a good indicator of vascular stenosis. Also, $v_{max}$ is used to estimate the pressure drop across a stenosis based on the Bernoulli equation.

In the conventional ultrasound scanner shown in FIG. 1, the Doppler spectrogram is computed via the FFT. Various methods have been developed to automatically trace the $f_{max}$ waveform over a white noise background. A summary of these methods for detection of $f_{max}$ in the FFT spectrogram can be found in an article by Mo et al. entitled "Comparison of Four Digital Maxi-mum Frequency Estimators for Doppler Ultrasound," Ultrasound Med. Biol., Vol. 14, pp. 355–363 (1988). For implementation on a real-time Doppler system, similar techniques have been proposed (see, e.g., U.S. Pat. No. 5,287,753) for compressed Doppler spectrograms with 6–8 bits of display dynamic range. However, it has been reported that the maximum velocity estimates can be 10–60% higher than the actual maximum velocity within the sample volume (see Daigle et al., "Overestimation of Velocity and Frequency Values by Multi-Element Linear Array Probes," J. Vasc. Technology, Vol. 14, pp. 206–213 (1990) and Hoskins et al., "Velocity Estimation Using Duplex Scanners," Ultra-sound Med. Biol., Letter to the Editor, Vol. 17, pp. 195–198 (1991)). Besides statistical and operator's variability, a significant portion of this error can be attributed to intrinsic Doppler spectral broadening. This problem is compounded by the fact that the amount of intrinsic spectral broadening is generally dependent on beamforming as well as signal processing parameters.

The published literature on Doppler spectral broadening can be divided into two distinct camps. One camp considered only the spectral broadening associated with a finite bandwidth pulse, which is a manifestation of the fundamental tradeoff between spatial (time) and velocity (frequency) resolution. The other camp assumed narrowband excitation (CW Doppler or pulsed Doppler with a long range cell) and focused on diffraction broadening. A geometric explanation of diffraction broadening is that the rays emanating from the different transducer array elements form different angles with the scatterer velocity vector. Diffraction broadening is also sometimes described as a finite transit time effect for scatterers moving across the sound beam.

Most, if not all, of the spectral broadening reduction or correction methods which have been proposed actually deal only with the diffraction component. The simplest method is to reduce the transducer active aperture at the expense of decreased spatial resolution and sensitivity, as disclosed in the Daigle et al. and Hoskins et al. references cited above. The theory of Newhouse et al., set forth in "The Dependence of Ultrasound Doppler Bandwidth on Beam Geometry," IEEE Trans. Sonics and Ultrasonics, Vol. SU-27, pp. 50–59 (1980), has also been applied to correct the $f_{max}$ estimates for diffraction broadening. See, e.g., Winkler et al., "Correction of Intrinsic Spectral Broadening Errors in Doppler Peak Velocity Measurements Made with Phased Sector and Linear Array Transducers," Ultrasound Med. Biol., Vol. 21, pp. 1029–1035 (1995); Newhouse et al., "Invariance of Doppler Bandwidth with Flow Axis Displacement," Proc. IEEE Ultrasonics Symp., pp. 1533–1536 (1990); Newhouse et al., "Study of Vector Flow Estimation with Transverse Doppler," Proc. IEEE Ultrasonics Symp., pp. 1259–1263 (1991); Tortoli et al., "Invariance of the Doppler Bandwidth with Range Cell Size Above a Critical Beam-to-Flow Angle," IEEE Trans. Ultrason., Ferroelec. and Freq. Control, Vol. UFFC-40, pp. 381–386 (1993). In U.S. Pat. No. 5,606,972, three additional methods have been proposed: (1) perform frequency-to-velocity conversion based on the smallest Doppler angle formed between the outermost element of the active aperture and the flow axis; (2) deconvolve the Doppler spectrum by an array distortion function; and (3) use Doppler reference signals for each element of the array which are a function of the position of the individual elements in the array aperture. The first method had been described earlier by Hoskins et al. The second method utilizes the theory of Newhouse et al. and assumes the actual velocity spread is very small—which may not be true for larger sample volumes. The third method requires a beamformer which is significantly more complex than those used for conventional methods.

Besides bandwidth and diffraction broadening, there is a third source of intrinsic spectral broadening referred to as analysis time broadening, which represents the frequency resolution corresponding to a finite FFT data window. The width of this data window is usually chosen to be around 10 msec, which is a compromise between frequency resolution and flow stationarity considerations. For a 10-msec window, analysis time broadening is usually small relative to bandwidth and diffraction broadening.

The study by Wilson ("Description of Broad-Band Pulsed Doppler Ultrasound Processing Using the Two-Dimensional Fourier Transform," Ultrasonic Imag., Vol. 13, pp. 301–315 (1991)) is perhaps the only one that has addressed all three types of intrinsic spectral broadening. This work, which is based on two-dimensional FFT analysis, gives an explicit expression for each type of broadening. However, it does not show whether or how the three types might interact with one another. It was only speculated that the total effect may be given by the square root of the sum of squares of the three types of broadening, as though they represent the standard deviation of independent random variables.

SUMMARY OF THE INVENTION

The present invention is a method of calibrating Doppler time-velocity waveforms obtained using a duplex ultrasound scanner. In accordance with the invention, a spectral broadening error margin for the maximum velocity waveform is determined based on a unified theory of intrinsic spectral broadening for pulsed Doppler signals. The error margin is colorized or highlighted in the Doppler waveform display.

In particular, the method of the invention corrects $f_{max}$ for all three sources of intrinsic spectral broadning. The unified spectral broadening theory on which the method is based is applicable to any sample volume size and orientation, single element transducers or multi-element arrays, with or without beam steering. This unified theory can be developed in either the frequency domain or time/spatial domain. In accordance with the preferred embodiment, the time/spatial domain is used.

BRIEF DESCRIPTION OF THE DRAWINGS

FIG. 2A is a schematic illustrating the geometry of insonation in relation to an x-z coordinate system for the case where the maximum velocity vector passes through the center of the sample volume from end to end.

FIG. 2B is a schematic illustrating the geometry of insonation in relation to an x-z coordinate system for the case where the maximum velocity vector passes through the center of the sample volume from side to side.

FIG. 3 is a graph showing a method for displaying the spectral broadening error margin in accordance with the invention for conventional grey-scale Doppler power spectrograms.

DETAILED DESCRIPTION OF THE PREFERRED EMBODIMENTS

Figure 1:
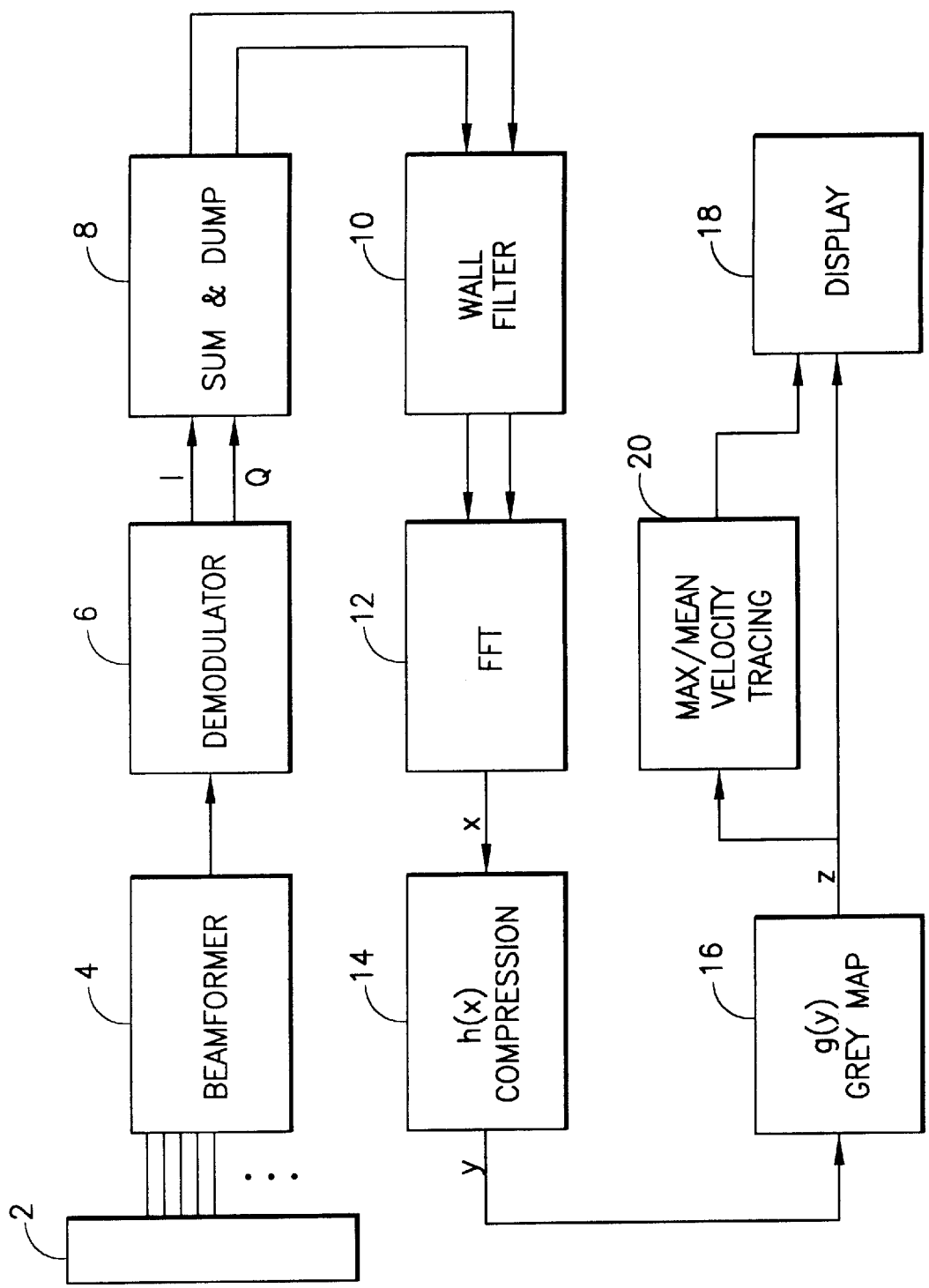
FIG. 1 is a block diagram showing the signal processing chain for a conventional spectral Doppler mode with automatic maximum and/or mean velocity waveform tracing. I and Q denote the in-phase and quadrature components of the demodulated signal.

The preferred embodiment of the invention corrects $f_{max}$ for all three sources of intrinsic spectral broadening. In what follows, the unified spectral broadening theory is developed in the time/spatial domain. The scan geometry is illustrated for the case where the maximum velocity vector passes through the center of the sample volume from end to end in FIG. 2A and for the case where the maximum velocity vector passes through the center of the sample volume from side to side in FIG. 2B.

The basic assumptions of the unified spectral broadening theory are the following:

1) All the physical processes that define the Doppler sample volume are linear.
2) Spectral broadening due to any out-of-plane (y-direction) motion is negligibly small.
3) The F-number (range/aperture ratio) is sufficiently large such that the lateral (x-direction) and axial (z-direction) sensitivity functions within the sample volume are independently governed by diffraction and by the received signal and subsequent filtering processes, respectively.
4) The sample volume is formed within the focal zone of the beam, within which the lateral sensitivity function is independent of z.
5) The maximum velocity vector passes through the center of the sample volume from end to end (as shown in FIG. 2A) or from side to side (as shown in FIG. 2B).
6) The effect of tissue attenuation on the received pulse shape does not vary significantly over the range of interest.

First, the error due to bandwidth broadening is calculated for an idealized, non-diffracting beam. For a linear system (Assumption 1) the transmitted voltage waveform, two-way transducer impulse response, bulk tissue loss and the low pass filters in the demodulator can be rolled into a two-way system transient of duration P. Strictly speaking, this system transient is a function of depth due to tissue attenuation effects. However, for a particular probe, we will simply use the system transient corresponding to the average depth of interest (Assumption 6).

The axial sensitivity function $A_L(z)$ is given by the system transient convolved with a rectangular window of duration T (i.e., the "range gate"). This moving average operation yields $A_L(z)$ with a full length of $$L_{full} = c(P+T)/2 \tag{1}$$

Note that $L_{full}$ is generally greater than the user-select sample volume length L (see FIG. 2A), which is typically defined by the −20 dB points from the peak of $A_L(z)$.

Attention will be focused on the fastest scattering particles moving at velocity $v_{max}$ through the central portion of the sample volume 24 (FIGS. 2A and 2B and Assumption 5). That is, depending on θ, these particles are moving through the sample volume from side to side or from end to end, with an axial velocity component $v_z = v_{max} \cos \theta$. Whereas the frequency of the backscattered wave from these particles is shifted from the transmit carrier frequency by an amount $$f_{max} = 2f_0(v_{max}/c) \cos \theta = 2f_0 v_z/c \tag{2}$$

the amplitude of the received signal is modulated by $A_L(t)$, in which $t = z/v_z$. Consequently, the Doppler signal sampled at the PRF contains a spread of frequencies corresponding to the spectrum of $A_L(t)$. Since the duration of $A_L(t)$ is $L/v_z$, the width of its spectrum is $$\Delta f_L = K_L \frac{v_z}{L} \tag{3}$$

where $K_L$ is a proportionality constant that depends on the shape of $A_L(t)$. The value of $K_L$ may range from unity to higher values depending on the ratio P/T. Equation (3) gives the sprectral broadening error on $f_{max}$ associated with the finite length of the sample volume. Dividing Eq. (3) by Eq. (2) yields a fractional error of $$\frac{\Delta f_L}{f_{max}} = K_L \frac{c}{2 f_o L} \tag{4}$$

which is independent of $v_z$ and θ. This represents the minimum achievable error for a given sample volume size in pulsed Doppler measurements. For $K_L = 1$, Eq. (4) reduces to the expression obtained by Kristoffersen et al., "A Time-Shared Ultrasound Doppler Measurement and 2-D Imaging System," IEEE Trans. Biomed. Engng., Vol. BME-35, pp. 285–295 (1988), for bandwidth broadening.

Next the error due to bandwidth and diffraction broadening is calculated. For θ>0, the same scattering particles are also moving across the beam at velocity $v_x = v_{max} \sin \theta$. The above analysis assumes that the two-way lateral sensitivity profile $A_W(x)$ is uniform (within the sample volume). In reality, due to beam diffraction, it can vary significantly with x and has a width that can be defined by W=Fλ, where F is the F-number of the beamformer and λ is the ultrasound wavelength. This means that the received signal from the fastest moving particles is further modulated by $A_W(t)$, where $t = x/v_x$. Since the width of $A_W(t)$ is $W/v_x$, lateral motion across a nonuniform beam profile causes the Doppler spectrum to be broadened by an amount $$\Delta f_W = K_W \frac{v_x}{W} \tag{5}$$

where $K_W$ is a proportionality constant that varies with the shape of $A_W(t)$. Assumptions (3) and (4) imply that the $A_W(x)$ within the sample volume is given by the magnitude of the product of the Fourier transform of the transmit and that of the receive array apodization function. As an example, for a rectangular aperture with flat transmit and receive apodization functions, $A_W(x)$ is of the form $\text{sinc}^2(x/W)$ for which W=Fλ represents the −7.8 dB width and the corresponding $K_W = 1$. If a tapered apodization function is used without altering the active aperture size, the beamwidth at the focal zone will be slightly larger. As a result, diffraction broadening will be reduced and $K_W < 1$. If the transmit and receive apertures are not the same, then F should be treated as an effective F-number such that W=Fλ.

Using Eq. (2) and W=Fλ, Eq. (5) can be written as $$\frac{\Delta f_W}{f_{max}} = K_W \frac{\tan \theta}{2F} \tag{6}$$

which indicates that the fractional diffraction broadening error is dependent on the insonation angle. As expected, if θ=0 (no lateral motion), there is no diffraction broadening. Note that for $K_W = 1$, Eq. (5) is the same as Newhouse et al.'s (1980) expression for a long sample volume (no bandwidth broadening).

In general, for a sample volume of arbitrary size and for any θ, the received signal from the fastest moving scatterers is amplitude modulated by both $A_L(t)$ and $A_W(t)$. Since these particles are assumed to be passing through the center of the sample volume (Assumption 5), the peaks of $A_L(t)$ and $A_W(t)$ should coincide. Under this condition, the energy spectrum of $A_L(t)A_W(t)$ is given by the convolution of their individual spectra. As a result, the total normalized broadening is equal to the algebraic sum of Eqs. (4) and (6) as follows:

$$\frac{\Delta f_L + \Delta f_W}{f_{max}} = K_L \frac{c}{2 f_o L} + K_W \frac{\tan \theta}{2F} \tag{7}$$

In practice the sample volume position is usually adjusted until the Doppler waveform appears most prominent in the display. This occurs when the central, most sensitive region of the sample volume coincides with the location of the maximum velocity vectors. If this assumption is not true, that is, if the fastest scatterers move through the sample volume from end to side or from side to end, then the resultant Doppler spectra may suffer more spectral broadening than specified by Eq. (7). Nevertheless, Eq. (7) would still represent a good estimate of the minimum error margin due to spectral broadening.

While Eq. (7) specifies the width of the Doppler power spectral density corresponding to the largest velocity component, when the FFT of the Doppler signal of duration $T_{FFT}$ is taken, the resultant power spectrum will be further broadened by an amount proportional to $1/T_{FFT}$ but independent of $f_{max}$. If the data window is rectangular, the analysis time broadening is exactly $1/T_{FFT}$. In general, using Eq. (7), the total amount of broadening becomes $$\Delta f = \left[ K_L \frac{c}{2f_oL} + K_W \frac{\tan\theta}{2F} \right] f_{max} + K_T \frac{1}{T_{FFT}} \quad (8)$$

where $K_T$ is a constant that depends on the shape of the data window. The total broadening is given by the algebraic sum of the individual components. Note that if some post-FFT spectral smoothing is performed to reduce speckle, then $K_T$ should be increased to reflect the effective spectral window width.

In practice, to obtain an estimate of $v_{max}$, angle correction is usually applied to the apparent maximum Doppler frequency $f_{max}'=f_{max}+\Delta f$. From Eq. (8) the true maximum frequency can be written in terms of the apparent maximum frequency as follows:

$$f_{max} = \frac{f'_{max} - K_T/T_{FFT}}{1 + [cK_L/(2f_0L) + K_W\tan\theta/(2F)]} \quad (9)$$

Figure 4:
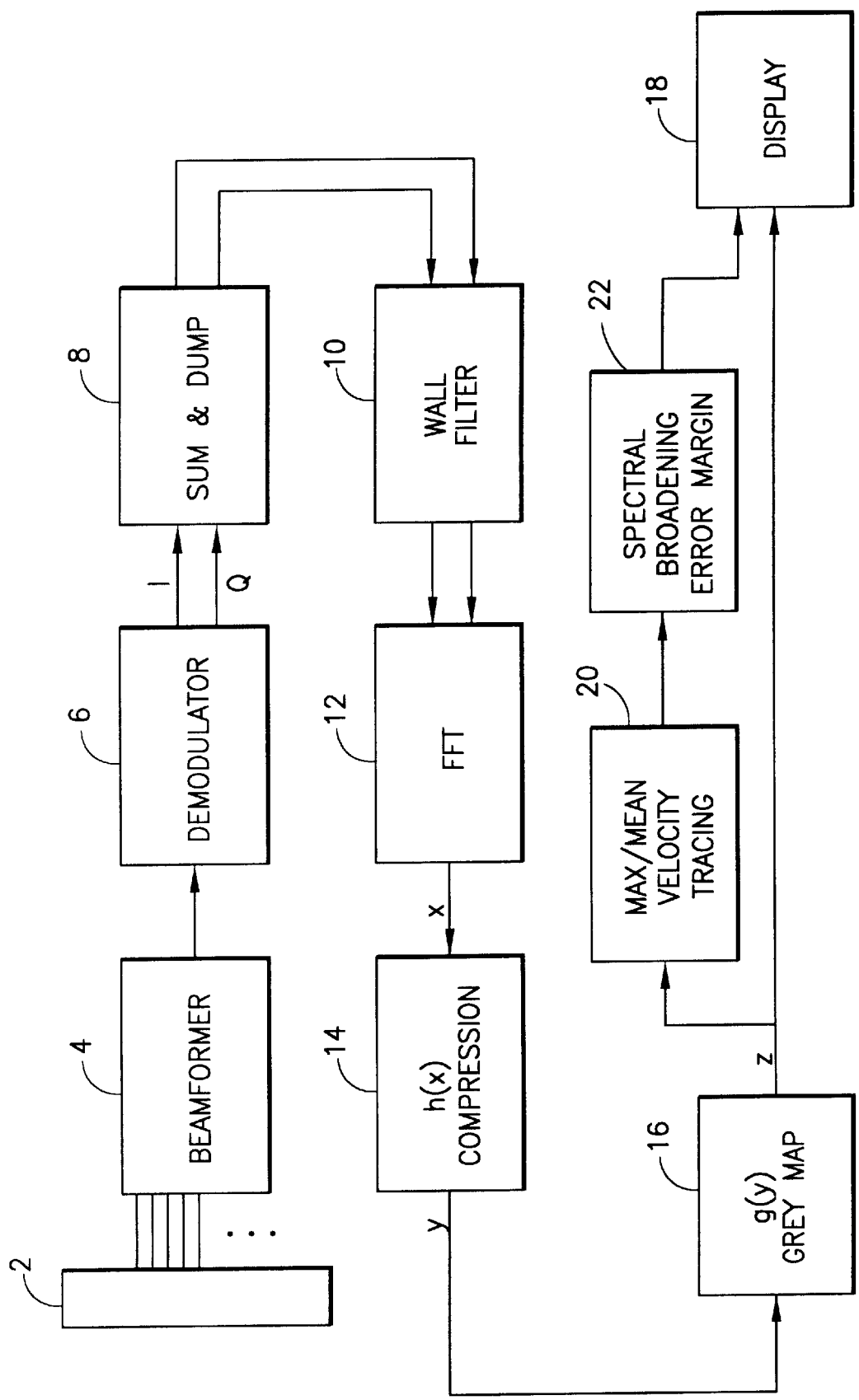
FIG. 4 is a block diagram showing the signal processing chain for a spectral Doppler mode with estimation and display of the spectral broadening error margin in accordance with the present invention.

At any instant of time in a Doppler spectrogram, the spectral broadening error margin SBEM=$f_{max}'-f_{max}'$ is given by $$SBEM = f'_{max} - \frac{f'_{max} - K_T/T_{FFT}}{1 + [cK_L/(2f_0L) + K_W\tan\theta/(2F)]} \quad (10)$$

where $\theta$ is the user-specified beam-to-flow angle estimate; L is the user-specified sample volume length; $K_L$ is a constant that depends on the shape of the axial sensitivity profile; F is the effective F-number of the Doppler transmit-receive beamformer; $K_W$ is a constant that depends on the shape of the lateral sensitivity profile; $T_{FFT}$ is the duration of the FFT data window; and $K_T$ is a constant that depends on the shape of the FFT data window. Note that while $\theta$ and L are user-specified in a duplex instrument, all of the remaining constants should be known a priori for a given Doppler beamformer and processor, and for a given application (attenuation effects associated with the average depth of insonation). The values of the K constants for different sample volume sizes and angles can be stored in a lookup table, for example. Thus, Eq. (10) can be easily implemented in software on a digital Doppler processor. Such a system is depicted in FIG. 4. In accordance with the preferred embodiment, FFT means 12, compression means 14, grey mapping means 16, velocity tracing means 20 and spectral broadening error margin means 22 are all incorporated in a digital Doppler processor.

As mentioned earlier, the display dynamic range of the Doppler spectrogram is typically limited to 6–8 bits in a conventional digital ultrasound scanner. The above spectral broadening error margin analysis assumes that the tail end of the broadened spectrum at each time instant can be observed and traced in the Doppler spectral display. If the spectral Doppler SNR is too weak, such that the tail end of the spectrum is buried in the noise floor, then the noise floor will have effectively masked out spectral broadening. In that case the real problem is one of sensitivity and not so much accuracy. Similarly, if for some reason the Doppler display dynamic range is set too low, it will also reduce the observable spectral broadening. It would not be possible to apply Eq. (10) to a spectrogram that has been artificially clipped at the low end of the amplitude range.

For the above reasons, some simple tests of the Doppler spectral SNR and display dynamic range should be performed before applying Eq. (10) to estimate spectral broadening error margin. For those skilled in the art it would be obvious that many variations of these tests are possible. For example, one can check to make sure that the mean noise floor level is at least 25 dB below the peak amplitude for each spectral line, and that the display dynamic range is at least as large. These tests should not involve much additional computation since some mean noise floor estimate is often derived from the upper pure-noise region in the spectrogram anyway for the purpose of tracing $f_{max}'$.

For an instantaneous spectrum it is obvious that both $f_{max}'$ (or the corresponding $v_{max}'$) and the corrected value $f_{max}$ can be displayed. To avoid confusion, however, a spectral broadening error margin display method is proposed as illustrated in FIG. 3. The basic idea is to provide the user with a spectral broadening error margin switch in Doppler mode, such that when the switch is turned on, the spectral broadening error margin (indicated by "SBEM" in FIG. 3) in the greyscale Doppler spectrogram will be colorized or highlighted by some shading method. This signifies that all those frequencies/velocities within the colorized spectral broadening error margin are not likely to represent real velocities within the sample volume. The advantage of this display method is that while it provides a good visual impression of the size of the error, the user is still free to choose any maximum frequency within the colorized error band for diagnostic index calculations. Of course, this form of display can be generated in real time or in freeze mode, depending on the computing power of the Doppler processor. If the normal spectrogram is already displayed in color, the spectral broadening error margin can be highlighted in greyscale or using other obvious shading methods.

The foregoing preferred embodiments have been disclosed for the purpose of illustration. Variations and modifications will be readily apparent to those skilled in the art. All such variations and modifications are intended to be encompassed by the claims set forth hereinafter.

What is claimed is:

1. A method for displaying a spectral broadening error margin of a Doppler velocity-time waveform envelope, comprising the steps of:

transmitting pulses of ultrasound into a sample volume of ultrasound scatterers;

acquiring a multiplicity of successive samples of Doppler signals backscattered from said sample volume of ultrasound scatterers;

processing said Doppler signals to produce spectral line data representing velocity for continuous display of a succession of spectral lines during continuation of Doppler signal acquisition, the data for each spectral line comprising a multiplicity of frequency bins for different frequency intervals, each bin containing spectral power data for a respective frequency interval, the spectral power data in each bin for each spectral line being displayed as a scale in a respective pixel of a corresponding column of pixels on a display monitor;

for each spectral line, determining a spectral broadening error margin comprising errors due to bandwidth, diffraction and analysis time broadening; and displaying a graphical representation of the magnitude of the determined spectral broadening error for each spectral line on said display monitor.

2. The method as defined in claim 1, wherein said processing step comprises taking Fast Fourier Transforms (FFTS) over a data window of samples, and wherein the spectral broadening error margin is determined in accordance with an equation:

$$SBEM = f'_{max} - \frac{f'_{max} - K_T/T_{FFT}}{1 + [cK_L/(2f_0L) + K_W\tan\theta/(2F)]}$$

where θ is a beam-to-flow angle estimate; L is a sample volume length; $K_L$ is a constant that depends on a shape of an axial sensitivity profile; F is an effective F-number of a Doppler transmit-receive beamformer; $K_W$ is a constant that depends on a shape of a lateral sensitivity profile; $T_{FFT}$ is a duration of an FT data window; and $K_T$ is a constant that depends on a shape of said FT data window.

3. The method as defined in claim 1, wherein said step of displaying the determined spectral broadening error for each spectral line comprising highlighting a region below a Doppler velocity-time waveform envelope and corresponding to the determined spectral broadening error.

4. A system for displaying a spectral broadening error margin of a Doppler velocity-time waveform envelope, comprising:

means for transmitting pulses of ultrasound into a sample volume of ultrasound scatterers;

means for acquiring a multiplicity of successive samples of Doppler signals backscattered from said sample volume of ultrasound scatterers;

a display monitor comprising columns of pixels;

means for processing said Doppler signals to produce spectral line data representing velocity for continuous display of a succession of spectral lines during continuation of Doppler signal acquisition, the data for each spectral line comprising a multiplicity of frequency bins for different frequency intervals, each bin containing spectral power data for a respective frequency interval, the spectral power data in each bin for each spectral line being displayed as a scale in a respective pixel of a corresponding column of pixels on said display monitor;

means for determining a spectral broadening error margin for each spectral line, said spectral broadening error margin comprising errors due to bandwidth, diffraction and analysis time broadening; and means for displaying a graphical representation of the magnitude of the determined spectral broadening error for each spectral line on said display monitor.

5. The system as defined in claim 4, wherein said means for displaying the determined spectral broadening error for each spectral line comprises means for high-lighting a region below a Doppler velocity-time waveform envelope and corresponding to the determined spectral broadening error.

6. A system for displaying a spectral broadening error margin of a Doppler velocity-time waveform envelope, comprising:

a Doppler transmit-receive beamformer comprising means for transmitting pulses of ultrasound into a sample volume of ultrasound scatterers and means for acquiring a multiplicity of successive samples of Doppler signals backscattered from said sample volume of ultrasound scatterers;

a display monitor comprising columns of pixels;

means for processing said Doppler signals to produce spectral line data representing velocity for continuous display of a succession of spectral lines during continuation of Doppler signal acquisition, the data for each spectral line comprising a multiplicity of frequency bins for different frequency intervals, each bin containing spectral power data for a respective frequency interval, the spectral power data in each bin for each spectral line being displayed as a scale in a respective pixel of a corresponding column of pixels on said display monitor;

means for determining a spectral broadening error margin for each spectral line, said spectral broadening error margin comprising errors due to bandwidth, diffraction and analysis time broadening; and means for displaying a graphical representation of the magnitude of the determined spectral broadening error for each spectral line on said display monitor.

7. The system as defined in claim 6, wherein said processing means comprises a spectrum analyzer which takes Fast Fourier Transforms (FFTs) over a data window of samples, and the spectral broadening error margin is determined in accordance with an equation:

$$SBEM = f'_{max} - \frac{f'_{max} - K_T/T_{FFT}}{1 + [cK_L/(2f_0L) + K_W\tan\theta/(2F)]}$$

where θ is a beam-to-flow angle estimate; L is a sample volume length; $K_L$ is a constant that depends on a shape of an axial sensitivity profile; F is the effective F-number of said Doppler transmit-receive beamformer; $K_W$ is a constant that depends on a shape of a lateral sensitivity profile; $T_{FFT}$ is the duration of said FT data window; and $K_T$ is a constant that depends on the shape of said FT data window.

8. The system as defined in claim 6, wherein said means for displaying the determined spectral broadening error for each spectral line comprise means for high-lighting a region below a Doppler velocity-time waveform envelope and corresponding to the determined spectral broadening error.

9. A system for displaying a spectral broadening error margin of a Doppler velocity-time waveform envelope, comprising:

a transducer comprising a multiplicity of ultrasound transducing elements;

a display monitor comprising a multiplicity of pixels;

a computer programmed to perform the following steps:
(a) controlling said transducer to transmit pulses of ultrasound into a sample volume of ultrasound scatterers;
(b) controlling said transducer to acquire a multiplicity of successive samples of Doppler signals backscattered from said sample volume of ultrasound scatterers;
(c) processing said Doppler signals to produce spectral line data representing velocity for continuous display of a succession of spectral lines during continuation of Doppler signal acquisition, the data for each spectral line comprising a multiplicity of frequency bins for different frequency intervals, each bin containing spectral power data for a respective frequency interval, the spectral power data in each bin for each spectral line being displayed as a scale in a respective pixel of a corresponding column of pixels on said display monitor;
(d) for each spectral line, determining a spectral broadening error margin comprising errors due to bandwidth, diffraction and analysis time broadening; and
(e) controlling said display monitor to display a graphical representation of the magnitude of the determined spectral broadening error for each spectral line.

10. The system as recited in claim 9, wherein said processing step comprises taking Fast Fourier Transforms (FFTs) over a data window of samples, and wherein the spectral broadening error margin is determined in accordance with an equation:

$$SBEM = f'_{max} - \frac{f'_{max} - K_T/T_{FFT}}{1 + [cK_L/(2f_0 L) + K_W \tan\theta/(2F)]}$$

where $\theta$ is a beam-to-flow angle estimate; L is a sample volume length; $K_L$ is a constant that depends on a shape of an axial sensitivity profile; F is an effective F-number for Doppler transmit-receive beamforming; $K_W$ is a constant that depends on a shape of a lateral sensitivity profile; $T_{FFT}$ is the duration of said data window; and $K_T$ is a constant that depends on a shape of said data window.

11. The system as recited in claim 9, wherein said step of displaying the determined spectral broadening error for each spectral line comprises highlighting a region below a Doppler velocity-time waveform envelope and corresponding to the determined spectral broadening error.

\* \* \* \* \*

UNITED STATES PATENT AND TRADEMARK OFFICE
CERTIFICATE OF CORRECTION

PATENT NO. : 6,176,143 B1
DATED : January 23, 2001
INVENTOR(S) : Larry Y.L. Mo et al.

It is certified that error appears in the above-identified patent and that said Letters Patent is hereby corrected as shown below:

Column 8, line 65 change "(FFTS)" to -- (FFTs) --.

Column 9, line 11, delete "FT".

Column 9, line 12, delete "FT".

Column 10, line 28, delete "FT".

Column 10, line 29, delete "FT".

Signed and Sealed this

Fifteenth Day of May, 2001

Attest:

NICHOLAS P. GODICI

Attesting Officer      Acting Director of the United States Patent and Trademark Office